United States Patent
Nakanishi et al.

(10) Patent No.: US 8,920,330 B2
(45) Date of Patent: Dec. 30, 2014

(54) BODY COMPRESSOR AND BLOOD PRESSURE MEASUREMENT APPARATUS

(75) Inventors: Takashi Nakanishi, Hachioji (JP);
Kazunari Takahashi, Morioka (JP);
Kenichi Matsumoto, Morioka (JP)

(73) Assignee: Citizen Systems Japan Co., Ltd., Nishitokyo-Shi, Tokyo (JP)

( * ) Notice: Subject to any disclaimer, the term of this patent is extended or adjusted under 35 U.S.C. 154(b) by 715 days.

(21) Appl. No.: 12/662,491

(22) Filed: Apr. 20, 2010

(65) Prior Publication Data
US 2010/0268100 A1   Oct. 21, 2010

(30) Foreign Application Priority Data

Apr. 21, 2009  (JP) ................. 2009-102682

(51) Int. Cl.
*A61B 5/02* (2006.01)
*A61B 5/022* (2006.01)
*A61B 5/00* (2006.01)

(52) U.S. Cl.
CPC ........... *A61B 5/02233* (2013.01); *A61B 5/6824* (2013.01)
USPC ........................ 600/499; 606/202; 606/203

(58) Field of Classification Search
CPC ........... A61B 5/02233; A61B 5/02141; A61B 17/135; A61B 17/1322; A61B 17/132
USPC .................... 600/499; 606/202, 203
See application file for complete search history.

(56) References Cited

U.S. PATENT DOCUMENTS

| 4,832,040 A | * | 5/1989 | Ruff ........................... 600/499 |
| 4,838,276 A | * | 6/1989 | Nagai et al. .................. 600/499 |
| 2010/0130877 A1 | | 5/2010 | Matsumoto et al. | |

FOREIGN PATENT DOCUMENTS

| JP | H01-104245 | 4/1989 |
| JP | 2-37605 | 3/1990 |
| JP | H05-115447 | 5/1993 |
| JP | H06-261866 | 9/1994 |
| JP | 2009-077824 | 4/2009 |

OTHER PUBLICATIONS

Japanese Patent Office, "Office Action for JP2011-129179", Dec. 24, 2012.
Chinese Patent Office, "Office Action for CN 201010166638.4", Feb. 17, 2013.

* cited by examiner

*Primary Examiner* — Etsub Berhanu
(74) *Attorney, Agent, or Firm* — Manabu Kanesaka

(57) ABSTRACT

A body compressor 1 is provided with a fluid bag 2, a band-like body 3 and a metal clip 4, wherein a fixed part 42 of the metal clip 4 is attached such that it is positioned above the outer surface of a skin pinching prevention tag part 5, and the skin pinching prevention tag part 5 has a reinforcing member 6 which allows the bending rigidity of a center-side part 51 and an intermediate part 52 to be higher than that of a front-side part 53.

6 Claims, 13 Drawing Sheets

BODY COMPRESSOR AND BLOOD PRESSURE MEASUREMENT APPARATUS

TECHNICAL FIELD

The present invention relates to a body compressor and a blood pressure measurement apparatus which have significantly improved attachability to a human body.

BACKGROUND ART

Recently, blood pressure monitors have come into wide use not only in, for example, hospitals but also in general households for the purpose of health care. The blood pressure monitors for the general households are typically automatic blood pressure monitors which are easy to operate.

Automatic blood pressure monitors based on various measurement methods and configurations have been developed, and an oscillometric electronic blood pressure monitor is one such blood pressure monitor. This oscillometric electronic blood pressure monitor detects a pulse wave superposed on the inner pressure of a fluid bag (generally called "air bag" since air is used), and calculates a blood pressure on the basis of changes in the amplitude of the pulse wave. This oscillometric electronic blood pressure monitor includes a body compressor (generally called a cuff) which is wound around the upper arm and has an air bag, a pressure sensor, a pump and an exhaust valve which are in communication with the air bag through a tube, an information processing unit which is connected to the pressure sensor, the pump and the exhaust valve, and an operation switch and a display which are connected to the information processing unit.

CONVENTIONAL EXAMPLES

In the above-mentioned automatic blood pressure measurement monitors, body compressors with various configurations have been used.

Next, an explanation is made on conventional body compressors with reference to the drawings.

FIG. 11 is a schematic reduced view of a conventional body compressor, in which (a) is a front development view and (b) is a rear development view; and FIG. 12 is a schematic view of a conventional body compressor, in which (a) is a view taken along the arrow G-G and (b) is a view taken along the arrow H-H.

In FIGS. 11 and 12, the body compressor 101 is provided with a fluid bag 2, a band-like body 130, a metal clip 4, a hook-and-loop fastener 133 or the like.
<Fluid Bag>

The fluid bag 2 is a substantially trapezoidal bag. The bag has an upper surface sheet which is provided with a joint 21 at almost the center thereof, a lower surface sheet, a welding part at which peripheral parts of these sheets are welded, or the like. This fluid bag 2 expands or shrinks when a fluid (normally air) is supplied or discharged. That is, when the body compressor 101 is wound around an upper arm 10 and air is supplied from the joint 21, the fluid bag 2 expands to compress the upper arm 10.
<Band-Like Body>

The band-like body 130 has a loop sheet 131 as an outer surface cover, an inner surface cover 135 or the like, and accommodates the fluid bag 2 by sandwiching the fluid bag 2 between the loop sheet 131 and the inner surface cover 135.

Each of the loop sheet 131 and the inner surface cover 135 has a substantially rectangular shape. The inner surface cover 135 is formed of a thin, soft and flexible cloth (normally, resin cloth) so that it is comfortable to the feel when it touches skin. The loop sheet 131 as the outer surface cover is thick and tough as compared with the inner surface cover 135, and does not have flexibility.

The loop sheet 131 and the inner surface cover 135 are stitched together at their peripheral parts with a thread 113 via a bias tape 134 with the fluid bag 2 or the like being interposed therebetween. Substantially in the middle in the longitudinal direction, the loop sheet 131 and the inner surface cover 135 are stitched together with a thread 12 along the arm axis direction. Moreover, the loop sheet 131 and the inner surface cover 135 have a smaller width on the other end side of the thread 12 than the width on the one end side such that they can easily fit to the shape of the upper arm 10.

The band-like body 130 has a skin pinching prevention tag part 150, which will be mentioned later, on the one end part thereof.
<Metal Clip>

The metal clip 4 is a piece of round steel which is formed in a substantially elliptical shape and has a hanging part 41 and a part 42 to be fixed (hereinafter referred to as the "fixed part 42"). The metal clip 4 is obliquely fixed to the vicinity of the one end part in the longitudinal direction of the band-like body 130 at an angle of about 80° from the lower side (the side nearer to the shoulder) of the band-like body 130. Thus, the body compressor 101 can be wound around even a muscular upper arm 10 substantially in close contact with each other.

As for the metal clip 4, as shown in FIG. 12(a), between the hanging part 41 and the fixed part 42 of the metal clip 4, one end of the folded band-like body 130 (the ends of the loop sheet 131 and the inner surface cover 135 stitched with a thread 113 via a bias tape 134) is passed through, whereby the band-like bodies 130 which are overlapped one on itself are stitched together with a thread 117 so as to allow the fixed part 42 to be interposed therebetween. That is, a pair of the band-like bodies 130 interposing the fixed part 42 therebetween serves as a fixing part, whereby the metal clip 4 is rotatably fixed. When the hanging part 41 is allowed to be rotated towards the one end part, the hanging part 41 abuts the front upper part of a front-side part 153 before it is brought in a horizontal state (that is, in a state where it is inclined at an angle of about 20°).
<Skin Pinching Prevention Tag Part>

A skin pinching prevention tag part 150 is formed in the vicinity of the one end part of the band-like body 130. That is, as shown in FIG. 12(a), the one end part of the band-like body 130 (the ends of the loop sheet 131 and the inner surface cover 135 stitched with the thread 113 via the bias tape 134) is folded back and is passed between the hanging part 41 and the fixed part 42 of the metal clip 4. This folding is conducted in a state that parts with a specific length of the band-like body 130 are positioned on the other end side of the fixed part 42 and on the other end side of the fixed part 42, respectively. In the parts of the band-like body 130 which are overlapped each other by the folding, the vicinity of the folding position is stitched with a thread 118, the vicinity of the two positions interposing the fixed part 42 is stitched with threads 117, and the vicinity of the front of the folded band-like body is stitched with a thread 116.

In this way, the skin pinching prevention tag part 150 consisting of a center-side part 151, an intermediate part 152 and a front-side part 153 is formed. The center-side part 151 is positioned substantially between the threads 117 on the center side of the fixed part 42 and the thread 116, and is formed of a pair of parts of the band-like body 130 which are overlapped each other. The intermediated part 152 is positioned between the pair of opposing threads 117, and is formed of the pair of parts of the band-like body 130 which rotatably fix the fixed part 42. Further, the front-side part 153 is positioned nearer to the one end side than the thread 117 on the one end side, and is formed of the pair of parts of band-like body 130 which are overlapped each other.

Here, the skin pinching prevention tag part 150 formed of two sheets of the band-like body 130 which are stitched together has a sufficiently larger bending rigidity (strength against bending) than a single sheet of the band-like body 130. As a result, when the body compressor 101 is wound around the upper arm 10, the front-side part 153 is inserted between skin and the inner surface cover 135, thereby to guarding the skin from entering a space in which the skin may be pinched (for example, a space between the hanging part 41 and the fixed part 42). The intermediate part 152 not only retains the fixed part 42 but also retains the front-side part 153 so as to allow the front-side part 153 to keep a state capable of guarding the skin (for example, so as to prevent the front-side part 153 from being folded at a part in the vicinity of the thread 117 on the one end side). Further, the center-side part 151, for example, supports the intermediate part 152 so as to prevent the intermediate part 152 from being folded at a part in the vicinity of the thread 117 on the other end side.

<Hook-and-Loop Fastener>

The body compressor 101 is provided with the hook-and-loop fastener 133 as a fixing means to fix the other end part of the band-like body 130 which is inserted into the metal clip 4 and which is folded back via the metal clip 4.

The hook-and-loop fastener 133 is formed of the above-mentioned loop sheet 131 and a hook sheet 32. The hook sheet 32 is substantially square, and is stitched with a thread 15 to the other end part of the loop sheet 131 as the outer surface cover.

<Explanatory Note Film>

An explanatory note film 138 is a substantially square film made of a resin, with warnings or the like which should be kept in mind when winding the body compressor 101 around the upper arm 10 being printed thereon. The periphery of this explanatory note film 138 is welded to the other end part of the inner surface cover 135 by a welding part 139. The explanatory note film 138 has a shape smaller than the hook sheet 32, and the welding part 139 thereof is positioned inside of the thread 15.

<Anti-Drop Member>

An anti-drop member 36 is a cylindrical member made of a resin, and is provided on the other end part of the hook sheet 32. That is, the anti-drop member 36 is accommodated between the loop sheet 131 and the inner surface cover 135 along the arm axis, and the position thereof is determined by means of a pair of opposing threads 14 which are located at the both sides in the longitudinal direction. This anti-drop member 36 can pass through the hanging part 41 and the fixed part 42 by elastic deformation, and the anti-drop member 36 which has passed then serves as a stopper. As a result, when the body compressor 101 is increased in diameter, the other end part of the band-like body 130 is not withdrawn from the metal clip 4, whereby handling properties of the body compressor 101 can be improved.

The above-mentioned body compressor 101 can be wound around even the muscular upper arm 10 substantially in close contact with each other. In addition, due to the presence of the skin pinching prevention tag part 150, there is no fear that skin is pinched, and handling properties during winding can be improved due to the presence of the anti-drop member 36.

Relating to the present invention, various technologies were disclosed.

For example, Patent Document 1 discloses an arm band for blood pressure monitors in which a plurality of bands for fastening a bag body in which an air bag is accommodated to the upper arm are provided in parallel in the longitudinal direction of the bag body. In the band of this document (bands 5a and 5b shown in FIG. 4), the front part thereof is passed through square iron bodies (12a and 12b) which serve as a metal clip. At a part nearer to the center than the square iron bodies, the front part and a part corresponding to this front part are attached to the bag body.

Patent Document 2 discloses a technology of an arm band for measuring a blood pressure comprising an arm band having an air bag in its inside, in which an insertion ring (metal clip) is provided such that it is spaced inwardly for a predetermined distance from one end of the arm band so as to allow the other end thereof to be inserted. In the insertion ring of this document (an insertion ring 12 shown in FIG. 3), one bar-like part (hanging part) is positioned on the outer surface of the arm band and the other bar-like part (fixed part) is attached to the inside of the arm band.

RELATED ART DOCUMENTS

Patent Documents

Patent Document 1: Japanese Utility Model Application No. S53-593
Patent Document 2: Japanese Utility Model Application No. S57-123107

SUMMARY OF THE INVENTION

Problems to be Solved by the Invention

However, in the case of the arm band for measuring blood pressure of Patent Document 2 or the above-mentioned body compressor 101, during winding around the upper arm 10, as shown in FIG. 13, when the other end part of the band-like body 130 is pulled in the pulling direction, the skin pinching prevention tag part 150 having a high bending rigidity behaves substantially similar to a rigid flat plate.

That is, in the body compressor 101, the rotation angle $\beta°$ of the metal clip 4 relative to the front-side part 153 is small, and hence, the tip of the front-side part 153 is pressed against the band-like body 130. At this time, depending on the force applied during pressing, friction force is generated between the front-side part 153 and the band-like body 130. Therefore, a user has to pull with strength larger than the friction force.

When the tip of the front-side part 153 is pressed against the band-like body 130, a part of the band-like body 130 which abuts the front-side part 153 is bent almost upwardly, and a part of the band-like body 130 which is hung on the hanging part 41 is bent almost downwardly. Accordingly, a user who pulls the other end part of the band-like body 130 has to pull it forcedly irrespective of a state in which the front-side part 153 is pressed against the band-like body. In particular, since a part of the band-like body 130 at which the explanatory note film 138 and the hook sheet 32 are positioned has a high bending rigidity, a force several times larger is required for pulling it as compared with a part without them.

Further, if the explanatory note film 138 is caught in the front-side part 153 or the hook sheet 32 is caught in the hanging part 41, the body compressor 101 may have loose contact with the upper arm 10 when a user pulls the other end part of the band-like body 130.

Meanwhile, the body compressor 101 has to be wound such that a joint 21 is positioned in a direction right above of the upper arm 10 with the palm thereof facing upward. Therefore, if such loose contact occurs, positioning has to be conducted again. Loose contact may occur when pulling is conducted with a force exceeding the above-mentioned friction force or pulling is conducted forcedly irrespective of a state in which the front-side part is pressed against the band-like body.

A user winds the body compressor with various procedures. As for the start of winding, some users start to wind in the left direction, some users start winding with the center part of the hook sheet 32 being hung on the hanging part 41, or some users conduct positioning of the joint 21 in a state where the hook sheet 32 has passed the hanging part 41, followed by pulling. That is, users conduct winding according to their own procedures (called "know-how" or "secrets"). For users who cannot follow their own procedures skillfully, winding the body compressor 101 around the left upper arm 10 only by the right hand is a significantly troublesome work. Under such circumstances, drastic improvement in attachability ((for example, lowered pulling strength, prevention of loose contact, smooth winding free from the feel that the front-side part of the skin pinching prevention tag part is pressed against the band-like body (hereinafter referred to as the "feel of resistance") or the feel that the explanatory note film or the hook sheet is caught in the front-side part or in the hanging part (hereinafter referred to as the "feel of hitching")) has been desired.

As stated in Patent Document 1, it is conceived that the metal clip is fixed such that it does not contact the band-like body to allow the metal clip to be distant from the band-like body, whereby friction force generated during winding can be reduced. However, if the metal clip is fixed in such a manner, the rigidity of the skin pinching prevention tag in the vicinity of the fixing position of the metal clip becomes insufficient. As a result, a problem arises that, when the band-like body is attached to the arm, the skin pinching prevention tag is folded in the opposite direction, and cannot function as a skin pinching prevention tag.

The present invention has been made in order to solve the above-mentioned problems associated with conventional technologies, and an object thereof is to provide a body compressor and a blood pressure measurement apparatus which can significantly improve attachability to a human body.

Means for Solving the Problem

In order to solve the above-mentioned problem, the body compressor of the present invention is a body compressor to be wound around a human body which comprises a fluid bag which expands and shrinks due to the supply and discharge of a fluid; a band-like body for accommodating the fluid bag; and a metal clip, which is provided on one end part of the band-like body, into which the other end part of the band-like body is inserted, wherein the metal flip is fixed to the band-like body at a metal clip-fixing position which is nearer to a center part of the band-like body for a predetermined distance from the one end part thereof in such a manner that it does not contact the outer surface of the band-like body, and the rigidity of the band-like body is higher in the metal clip-fixing position than in the one end part thereof.

The body compressor of the present invention is a body compressor to be wound around a human body which comprises a fluid bag which expands and shrinks due to the supply and discharge of a fluid; a band-like body for accommodating the fluid bag; and a metal clip, provided on one end part of the band-like body, into which the other end of the band-like body is inserted, wherein the metal clip is fixed to the band-like body such that it is away from the outer surface of the band-like body when a user pulls the other end part of the band-like body in order to attach the body compressor to his or her body; and the band-like body has a higher rigidity in a position where a fixing part for fixing the metal clip is installed to the band-like body than in the other end part thereof.

The blood pressure measurement apparatus of the present invention uses the above-mentioned body compressor.

Advantageous Effects of the Invention

According to the body compressor and the blood pressure measurement apparatus of the present invention, attachability (for example, lowered pulling strength, prevention of loose contact, smooth winding free from the feel of resistance or the feel of hitching) can be significantly improved when a body compressor is wound around a human body.

BEST MODE FOR CARRYING OUT THE INVENTION

First Embodiment of the Body Compressor

The first embodiment of the body compressor of the present invention will be explained hereinbelow with reference to the drawings.

Figure 1:
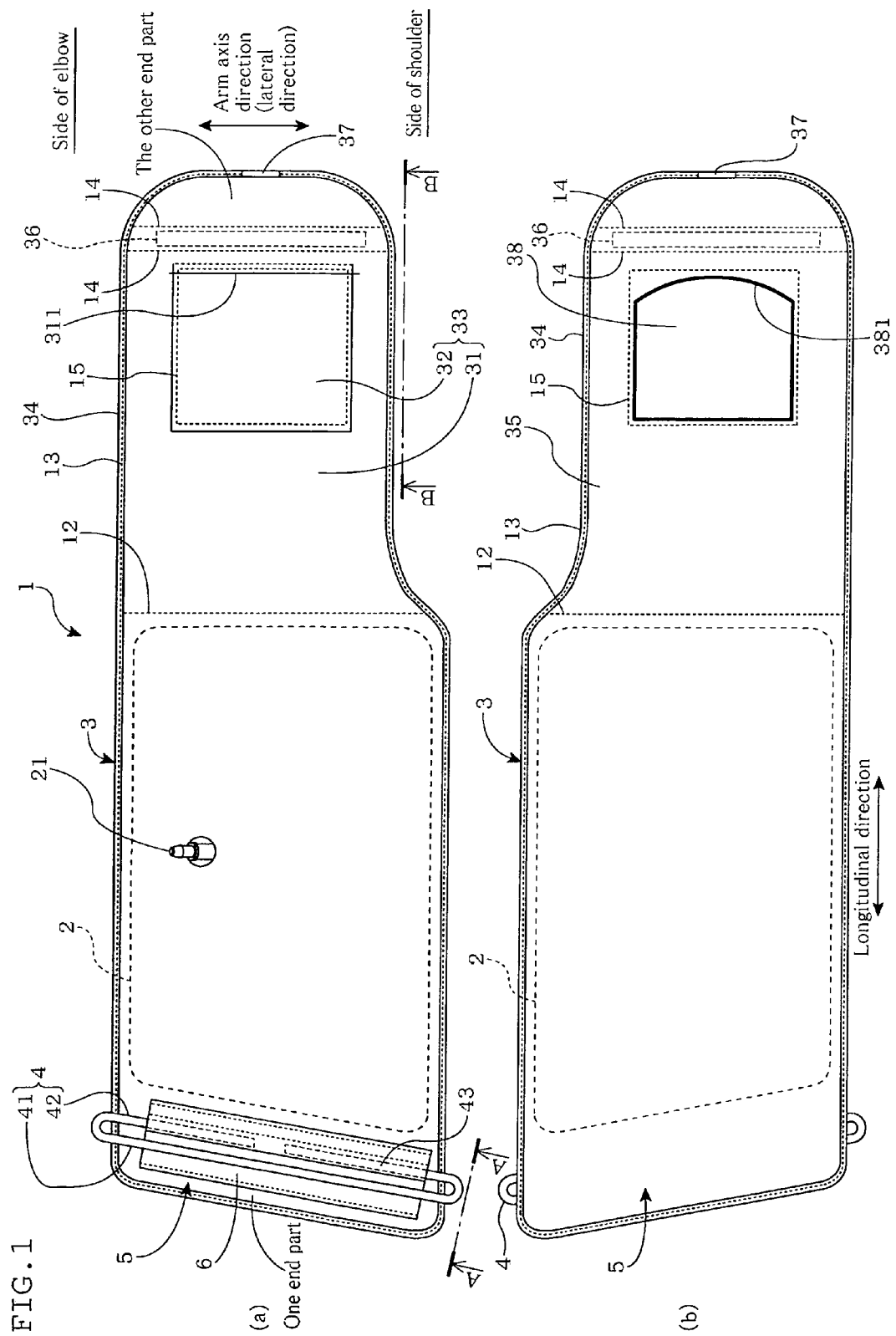
FIG. 1 is a schematic reduced view of the body compressor according to a first embodiment of the present invention, in which (a) is a front development view and (b) is a rear development view plan.

FIG. 1 is a schematic reduced view of the body compressor according to the first embodiment of the present invention, in which (a) is a front development view and (b) is a rear development view plan.

Figure 2:
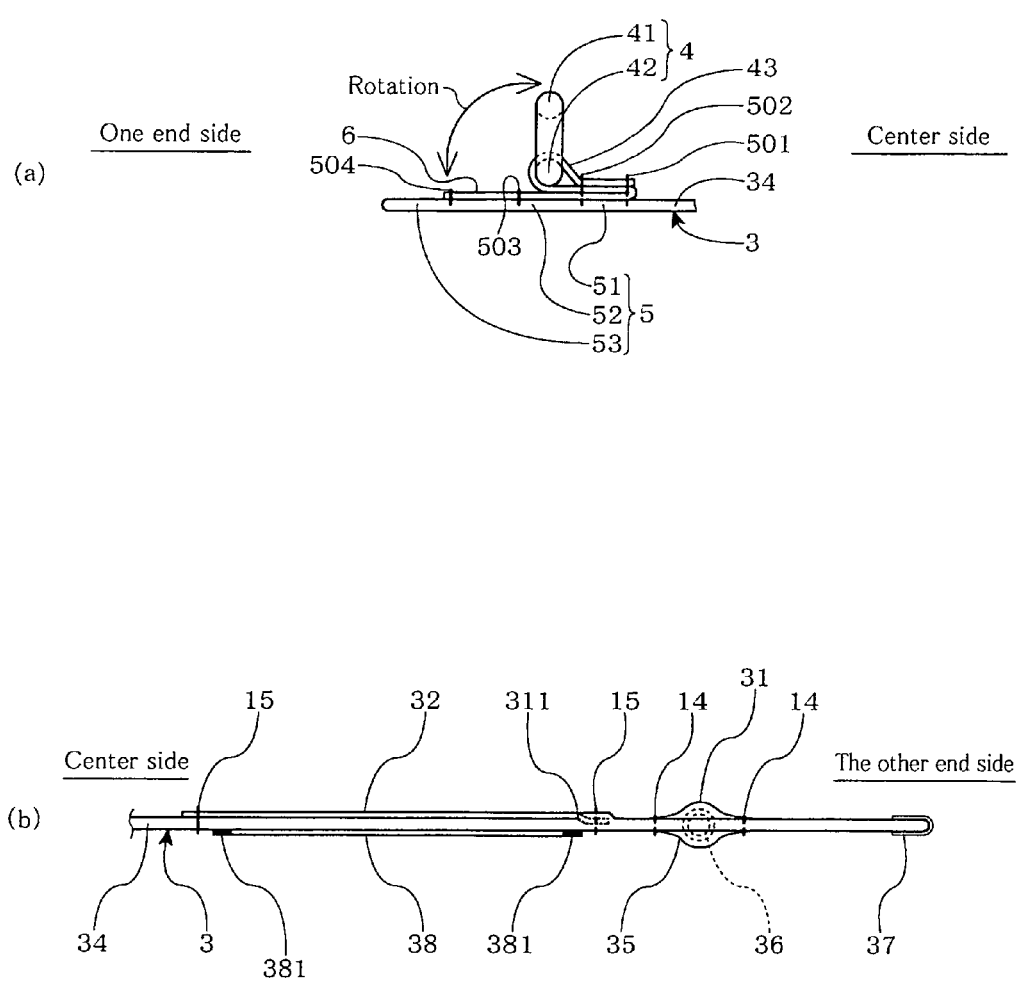
FIG. 2 is a schematic view of the body compressor according to the first embodiment of the present invention, in which (a) is a view taken along the arrow A-A and (b) is a view taken along the arrow B-B.

FIG. 2 is a schematic view of the body compressor according to the first embodiment of the present invention, in which (a) is a view taken along the arrow A-A and (b) is a view taken along the arrow B-B.

In FIGS. 1 and 2, the body compressor 1 is used as an arm band for an automatic blood pressure monitor (cuff), and is wound around the left upper arm 10 of a user. This body compressor 1 is provided with a fluid bag 2, a band-like body 3, a metal clip 4, a hook-and-loop fastener 33, or the like.

<Fluid Bag>

The fluid bag 2 is a substantially trapezoidal bag. The bag has an upper surface sheet which is provided with the joint 21 in substantially the middle thereof, a lower surface sheet, a welding part at which peripheral parts of these sheets are welded, or the like. This fluid bag 2 expands or shrinks when a fluid (normally air) is supplied or discharged. That is, when the body compressor 1 is wound around the upper arm 10 and air is supplied from the joint 21, the fluid bag 2 expands to compress the upper arm 10.

<Band-Like Body>

The band-like body 3 has a loop sheet 31 as an outer surface cover, an inner surface cover 35 or the like, and accommodates the fluid bag 2 by sandwiching the fluid bag 2 between the loop sheet 31 and the inner surface cover 35.

Each of the loop sheet 31 and the inner surface cover 35 is substantially rectangular. The inner surface cover 35 is formed of a thin, soft and flexible cloth (normally, resin cloth) so that it is comfortable to the feel when it touches the skin. The loop sheet 31 as the outer surface cover is thicker and tough as compared with the inner surface cover 35, and does not have flexibility. The outer surface of the loop sheet 31 serves as the outer surface of the band-like body 3.

The loop sheet 31 and the inner surface cover 35 are stitched together at their peripheral parts with a thread 13 via a bias tape 34 with the fluid bag 2 or the like being interposed therebetween. A metal fitting 37 for covering is provided on the other end part of the band-like body so as to cover the both ends of the stitched bias tape 34.

Substantially in the middle of the longitudinal direction, the loop sheet 31 and the inner surface cover 35 are stitched together with the thread 12 along the arm axis direction. Moreover, the loop sheet 31 and the inner surface cover 35 are smaller in width on the other end side of the thread 12 than on the one end side thereof so as to easily fit to the shape of the upper arm 10.

<Metal Clip>

The metal clip 4 is a piece of round steel which is formed in a substantially elliptical shape and has the hanging part 41 and the fixed part 42. The metal clip 4 is obliquely fixed to the vicinity of the one end in the longitudinal direction of the band-like body 3 at an angle of about 80° from the lower side (the side nearer to the shoulder) of the band-like body 3. Thus, the body compressor 1 can be wound around even a muscular upper arm 10 substantially in close contact with each other.

Further, as shown in FIG. 2(a), the metal clip 4 is fixed to the band-like body 3 by means of a fixing member 43 which is formed of the same member as that of the loop sheet 31, such that the fixed part 42 is positioned above the outer surface of the skin pinching prevention tag part 5 (in this embodiment, the upper surface of a reinforcing member 6).

That is, the fixing member 43 which has substantially the same width as that of the band-like body 3 is hung on the fixed part 42, and, at a position which is nearer to the center than the fixed part 42, the both ends of the fixing member 43 are stitched to the loop sheet 31 of the band-like body 3 with a thread 501 and a thread 502 via part of the reinforcing member 6. Due to such a configuration, when the hanging part 41 is rotated to the one end side, the hanging part 41 can be rotated until the metal clip 4 becomes almost parallel with the band-like body 3, and a gap with a small distance (a gap corresponding to the thickness of the fixing member 43) is formed between the rotated hanging part 41 and the reinforcing member 6. Therefore, when the body compressor 1 is wound around the upper arm 10, friction force generated between the band-like body 3 on the other end side which is to be hung on the hanging part 41 and the reinforcing member 6 or the band-like body 3 on the one end side (an intermediate part 52 or a front-side part 53) can be decreased, whereby a force required for pulling can be reduced.

<Reinforcing Member>

The reinforcing member 6 is made of the same member as that of the loop sheet 31, and has a rectangular shape having almost the same width as that of the band-like body 3. This reinforcing member 6 is a member which serves to allow the bending rigidity (or, simply referred to as "rigidity") of the skin pinching prevention tag part 5 on the central side (a center-side part 51 and an intermediate part 52) to be higher than the bending rigidity of the skin pinching prevention tag part 5 on the front side (a front-side part 53). The bending rigidity means a force against the bend.

In the reinforcing-member 6, the front part thereof on the one end side is positioned between a position at which the fixing member 43 is fixed (the position of the thread 502) and the front part on the one end side of the band-like body 3. That is, the reinforcing member 6 is stitched to the loop sheet 31 in such a manner that it is away from the one end part of the band-like body 3 for a predetermine distance and is parallel with the metal clip 4.

The fixing position of the metal clip 4 in the band-like body 3 is normally a position corresponding to the fixed part 42 or a position in the vicinity thereof.

In this embodiment, the end on the center side of the reinforcing member 6 and one end of the fixing member 43 are connected. That is, the fixing member 43 and the reinforcing member 6 are formed of a single sheet. The sheet is folded into two parts in substantially the middle thereof, and one part serves as the reinforcing member 6 and the other part serves as the fixing member 43. In this way, the number of components can be decreased, and operability of stitching can be enhanced, whereby the production cost can be reduced.

Regarding the above-mentioned stitching, one end of the reinforcing member 6 and the loop sheet 31 are stitched with a thread 504. The reinforcing member 6 and the loop sheet 31 are stitched with a thread 503 on the one end side of the fixed part 42. A pair of parts of the fixing member 43, which are overlapped each other, the reinforcing member 6 and the loop sheet 31 are stitched with a thread 502 on the center side of the fixed part 42. The both sides of the fixing member 43, the other end part of the reinforcing member 6 and the loop sheet 31 are stitched with a thread 501.

The reinforcing member 6 or the fixing member 43 is in the form of a sheet-like element (a loop sheet in this embodiment). The shape of the reinforcing member or the fixing member is not limited thereto. The reinforcing member or the fixing member may be a fabric member, for example.

<Skin Pinching Prevention Tag Part>

The skin pinching prevention tag part 5 has, from the center side to the one end side, a center-side part 51, an intermediate part 52 and a front-side part 53. The center-side part 51 is a part between the thread 501 and the thread 502, and is formed of the thread 501, the thread 502, the pair of parts of the fixing member 43, the reinforcing member 6 and the band-like body 3. The intermediate part 52 is a part between the thread 502 and the thread 504, and is formed of the thread 502, the thread 503, the thread 504, the reinforcing member 6 and the band-like body 3. Further, the front-side part 53 is a part nearer to the one end side than the thread 504, and is formed of the band-like body 3.

Therefore, the skin pinching prevention tag part 5 has a rigidity satisfying the following relationship: the rigidity of the center side part 51>the rigidity of the intermediate part 52>the rigidity of the front-side part 53. That is, in the skin pinching prevention tag part 5, since the center-side part 51 is reinforced with the fixing member 43, the reinforcing member 6 or the like, and the intermediate part 52 is reinforced with the reinforcing member 6 or the like, and the front-side part 53 is formed of the band-like body 3, it has bending rigidity differing in three stages.

<Hook-and-Loop Fastener>

The body compressor 1 is provided with the hook-and-loop fastener 33 as a fixing means to fix the other end of the band-like body 30 which is inserted into between the hanging part 41 and the fixed part 42 of the metal clip 4 and which is folded back via the hanging part 41.

The hook-and-loop fastener 33 is formed of the above-mentioned loop sheet 31 and a hook sheet 32. The hook sheet 32 is substantially square, and is stitched to the other end side of the loop sheet 31 as the outer surface cover with a thread 15.

Here, it is preferred that the hook sheet 32 of the hook-and-loop fastener 33 be provided on the outer surface on the other end side of the band-like body 3, and that the other end of the hook sheet 32 be accommodated within the outer surface cover (the loop sheet 31) of the band-like body 3. That is, in this embodiment, a notch 311 is provided in the loop sheet 31, and the other end of the hook sheet 32 is inserted into this notch 311. The loop sheet 31, the hook sheet 32 and the inner surface cover 35 are stitched with the thread 15.

In this way, the other end of the hook sheet 32 is accommodated within the loop sheet 31. Therefore, as compared with the body compressor 101, a problem that the other end of the hook sheet 32 is caught in the hanging part 41 of the metal clip 4 can be prevented, whereby the body compressor 1 can be wound around the upper arm 10 more smoothly.

Further, although not shown, it is preferred that the shape of the other end of the hook sheet 32 may be of a bended shape or a shape like an oblique side of a triangle. In this way, a problem that a step formed by the hook sheet 32 is caught in the hanging part 41 of the metal clip 4 can be further prevented, allowing the body compressor 1 to be wound around the upper arm 10 further smoothly.

<Explanatory Note Film>

An explanatory note film 38 is a film made of a resin, with warnings or the like which should be kept in mind when winding the body compressor 1 around the upper arm 10 being printed thereon. The explanatory note film 38 has a substantially square shape, having its portion on the other end side being curved. Due to such a configuration, when the body compressor 1 is wound around the upper arm 10, since the bending rigidity on the other end side of the band-like body 3 gradually increases, the body compressor 1 can be wound around the upper arm 10 more smoothly. The shape on the other end side is not limited to a curved shape. Although not shown, it may be a shape like an oblique side of a triangle, for example.

The periphery of this explanatory note film 38 is welded to the other and side of the inner surface cover 35 by a welding part 381. The explanatory note film 38 has a shape smaller than that of the hook sheet 32, and the welding part 381 thereof is positioned inside of the thread 15.

<Anti-Drop Member>

The anti-drop member 36 is a cylindrical member made of a resin, and is provided on the hook sheet 32 on the other end side. That is, the anti-drop member 36 is accommodated between the loop sheet 31 and the inner surface cover 35 along the arm axis, and the position thereof is determined by means of a pair of opposing threads 14 which are located at the both sides of the longitudinal direction. This anti-drop member 36 can pass between the hanging part 41 and the fixed part 42 by elastic deformation, and the anti-drop member 36 which has passed then serves as a stopper. As a result, when the body compressor 1 is increased in diameter, the other end part of the band-like body 3 is not withdrawn from the metal clip 4, whereby handling properties of the body compressor 1 can be improved.

The position at which the anti-drop member 36 is attached or the like are not limited to those as mentioned above. Although not shown, the anti-drop member 36 may be positioned nearer to the center than the hook sheet 32, or may be positioned on the center or the other end part of the hook sheet 32, for example.

Then, the operation of the body compressor 1 with the above-mentioned configuration will be explained with reference to the drawings.

Figure 3:
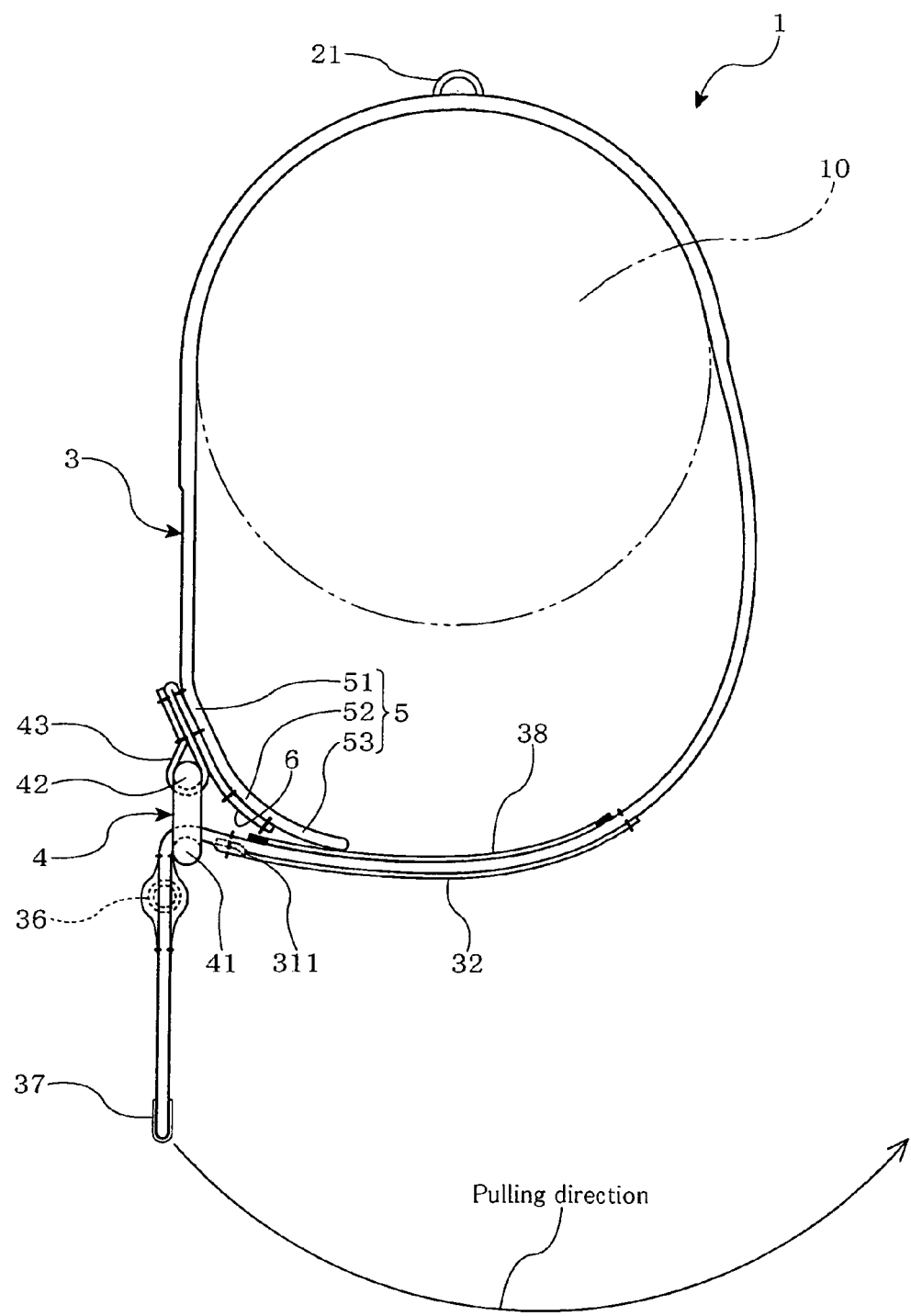
FIG. 3 is a schematic view of the body compressor according to the first embodiment of the present invention for explaining the operation at the start of winding.

FIG. 3 is a schematic view of the body compressor according to the first embodiment of the present invention for explaining the operation at the start of winding.

In FIG. 3, a user who tries to measure the body pressure, normally, passes the other end part of the band-like body 3 through the metal clip 4, and insert the left arm into the body compressor 1 of which the diameter has been increased. At this time, the user hangs the body compressor 1 on the upper arm 10 such that the joint 21 is positioned in a direction right above of the upper arm 10 with the palm being directed upwardly. Subsequently, the user pulls with his or her right hand the other end part of the band-like body 3 in the pulling direction.

At this time, when the front-side part 53 and the intermediate part 52 abut the explanatory note film 38, they are gradually curved corresponding to the slightly curved shape of the explanatory note film 38. That is, unlike the above-mentioned front-side part 153, the front-side part 53 and the intermediate part 52 are not strongly pressed against the band-like body 3, and bending occurs in sequence in such a manner that the front-side part 53, which has a lower bending rigidity, bends at first. Therefore, friction force generated between these parts and the explanatory note film 38 can be significantly decreased (decreased by one severalth of the friction force generated in the body compressor 101), whereby the force required for pulling the other end part of the band-like body 3 can be significantly decreased.

When the front-side part 53 and the intermediate part 52 abut the explanatory note film 38, they gradually bend corresponding to the explanatory note film 38. Therefore, unlike the front-side part 153, they do not cause the band-like body 3 to be bent almost upwardly. As a result, a problem that a user is annoyed by the feel of resistance caused by the pressing of the front-side part 53 or a user pulls forcedly irrespective of a state in which the front-side part 53 is pressed can be avoided.

In the skin pinching prevention tag part 5, the front of the front-side part 53 is positioned on the explanatory note film 38 in a state where the band-like body 3 is increased in diameter. That is, the skin pinching prevention tag part 5 has a length which is longer by about 30% of the skin pinching prevention tag part 150. Therefore, a problem that the front of the front-side part 53 is caught in a step of the explanatory note film 38 on the other end side can be avoided.

The skin pinching prevention tag part 5 has a rigidity satisfying the following relationship: the rigidity of the center-side part 51>the rigidity of the intermediate part 52>the rigidity of the front-side part 53. Therefore, the front-side part 53 which is most easily bent is supported by the intermediate part 52 such that it is not folded. The intermediated part 52 which is second most easily bent is supported by the center-side part 51 such that it is not folded. As a result, the skin pinching prevention tag part 5 which has a prolonged length can function as a tag for preventing skin from being pinched. Also, as mentioned above, the pulling strength can be decreased.

Further, as mentioned above, the other end part of the hook sheet 32 is accommodated within the loop sheet 31. As a result, problems that the end part of the hook sheet 32 is caught in the hanging part 41 of the metal clip 4, and the body compressor 1 suffers from loose contact with the upper arm 10 can be avoided, whereby the body compressor 1 can be wound around the upper arm 10 more smoothly.

Figure 4:
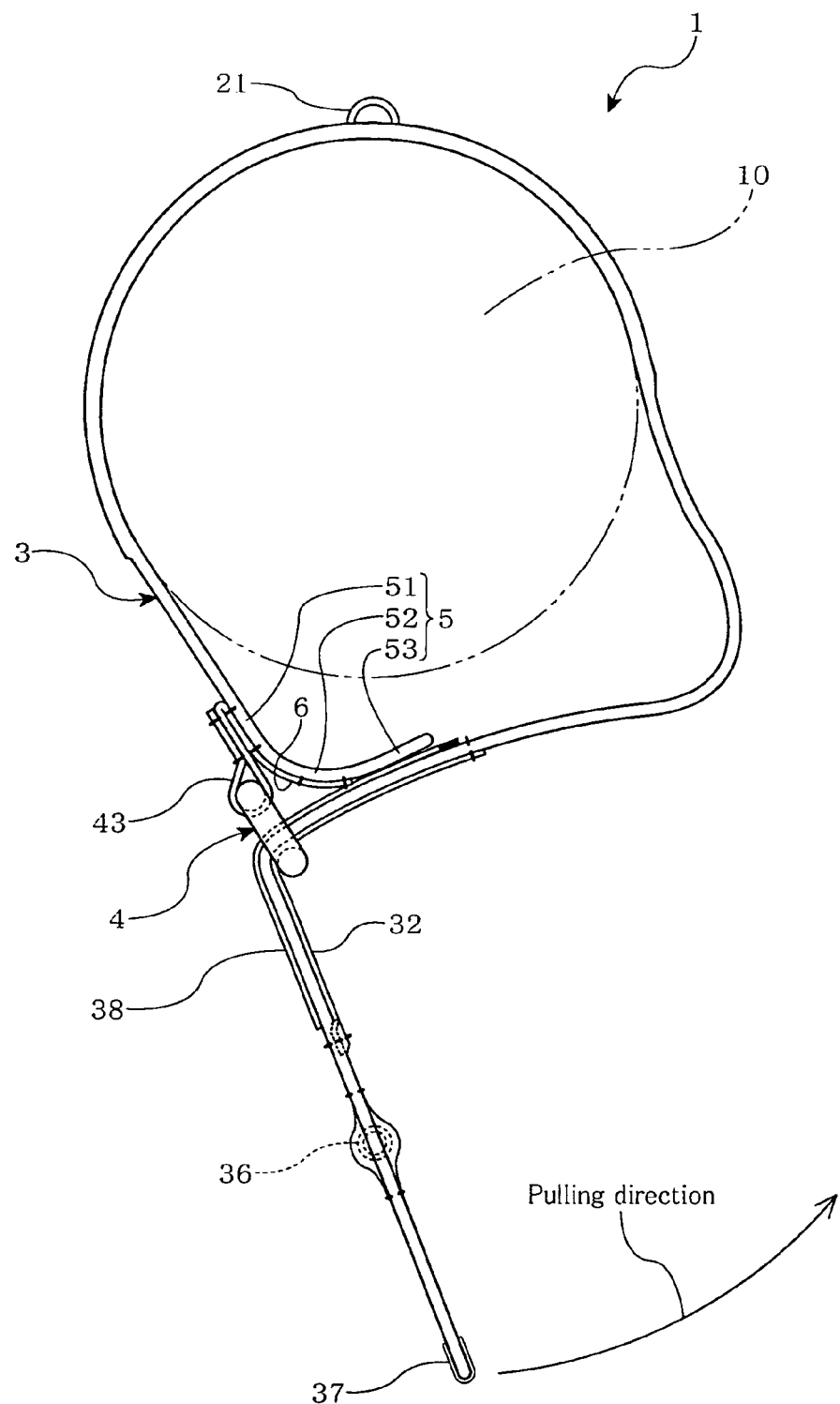
FIG. 4 is a schematic view of the body compressor according to the first embodiment of the present invention for explaining the operation during the winding.

FIG. 4 is a schematic view of the body compressor according to the first embodiment of the present invention for explaining the operation during the winding.

In the body compressor 1 shown in FIG. 4, the other end part of the band-like body 3 is pulled in the pulling direction. As compared with the skin pinching prevention tag part 5 shown in FIG. 3, the intermediate part 52 is bent largely, and the front-side part 53 does not undergo substantial bending. Here, the reinforcing member 6 corresponding to the intermediate part 52 is distant from the fixing part 43. As a result, the intermediate part 52 can be largely bent.

In this state, as mentioned above, in the body compressor 1, it is possible to decrease the force required for pulling the other end part of the band-like body 3. In addition, since the front-side part 53 and the intermediate part 52 are not folded, the skin pinching prevention tag part 5 can function as a tag for preventing skin from being pinched.

A part of the band-like body 3 corresponding to the hook sheet 32 (the hook sheet 32, part of the loop sheet 31, part of the inner surface cover 35 and the explanatory note film 38) has a large bending rigidity as compared with other parts. Therefore, although not shown, the part of the band-like body 3 corresponding to the hook sheet 32 may be bent downwardly in advance (for example, the radius of curvature of this part is rendered almost the same as the maximum radius of the upper arm 10). Due to such a configuration, the band-like body 3 which is hung on the hanging part 41 can be pulled easily.

Figure 5:
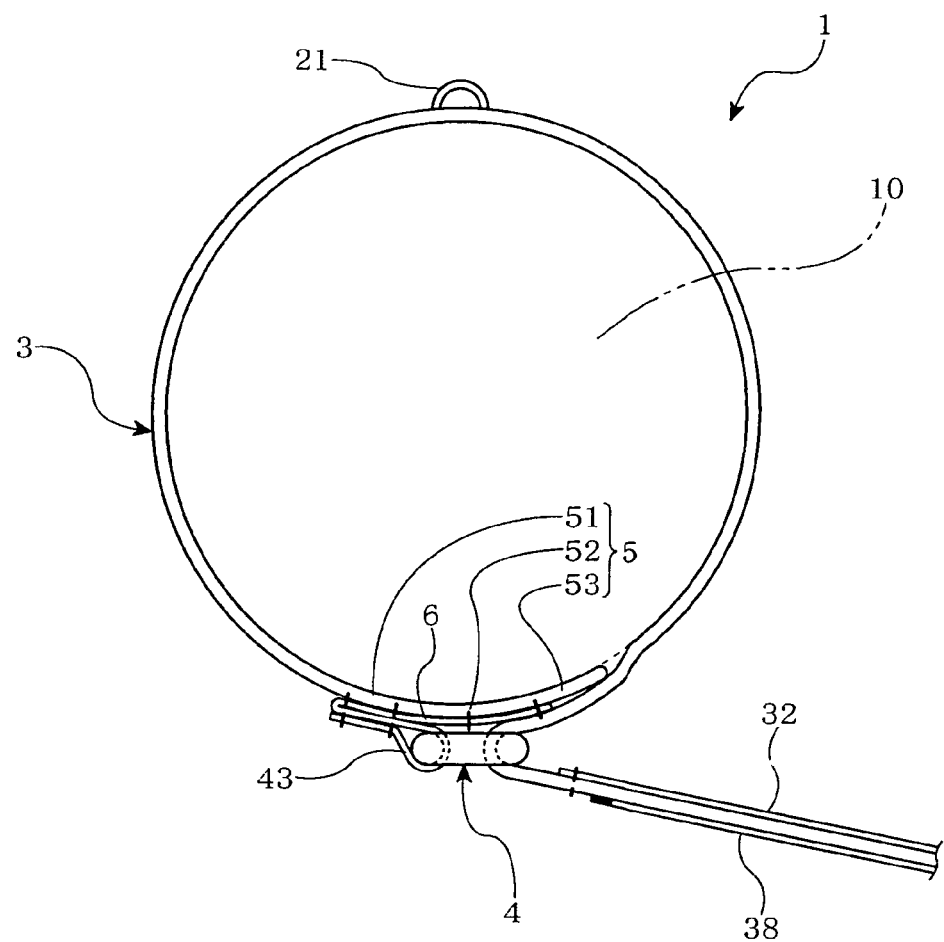
FIG. 5 is a schematic view of the body compressor according to the first embodiment of the present invention for explaining the operation at the time of completion of the winding.

FIG. 5 is a schematic view of the body compressor according to the first embodiment of the present invention for explaining the operation at the time of completion of the winding.

In FIG. 5, the body compressor 1 is almost wound around the upper arm 10, and the skin pinching prevention tag part 5 functions as a tag for preventing skin from being pinched. In the skin pinching prevention tag part 5 of this embodiment, since the front-side part 53 is formed of the loop sheet 31, the inner surface cover 35 or the like, the feel of fitting to the body can be improved as compared with the above-mentioned front-side part 153.

Although not shown, subsequently, the hook sheet 32 is joined to the loop sheet 31, whereby the winding operation is completed.

As mentioned above, according to the body compressor 1 of this embodiment, attachability (for example, lowered pulling strength, prevention of loose contact, smooth winding free from the feel of resistance or the feel of hitching, or the like) can be significantly improved.

Second Embodiment of the Body Compressor

Figure 6:
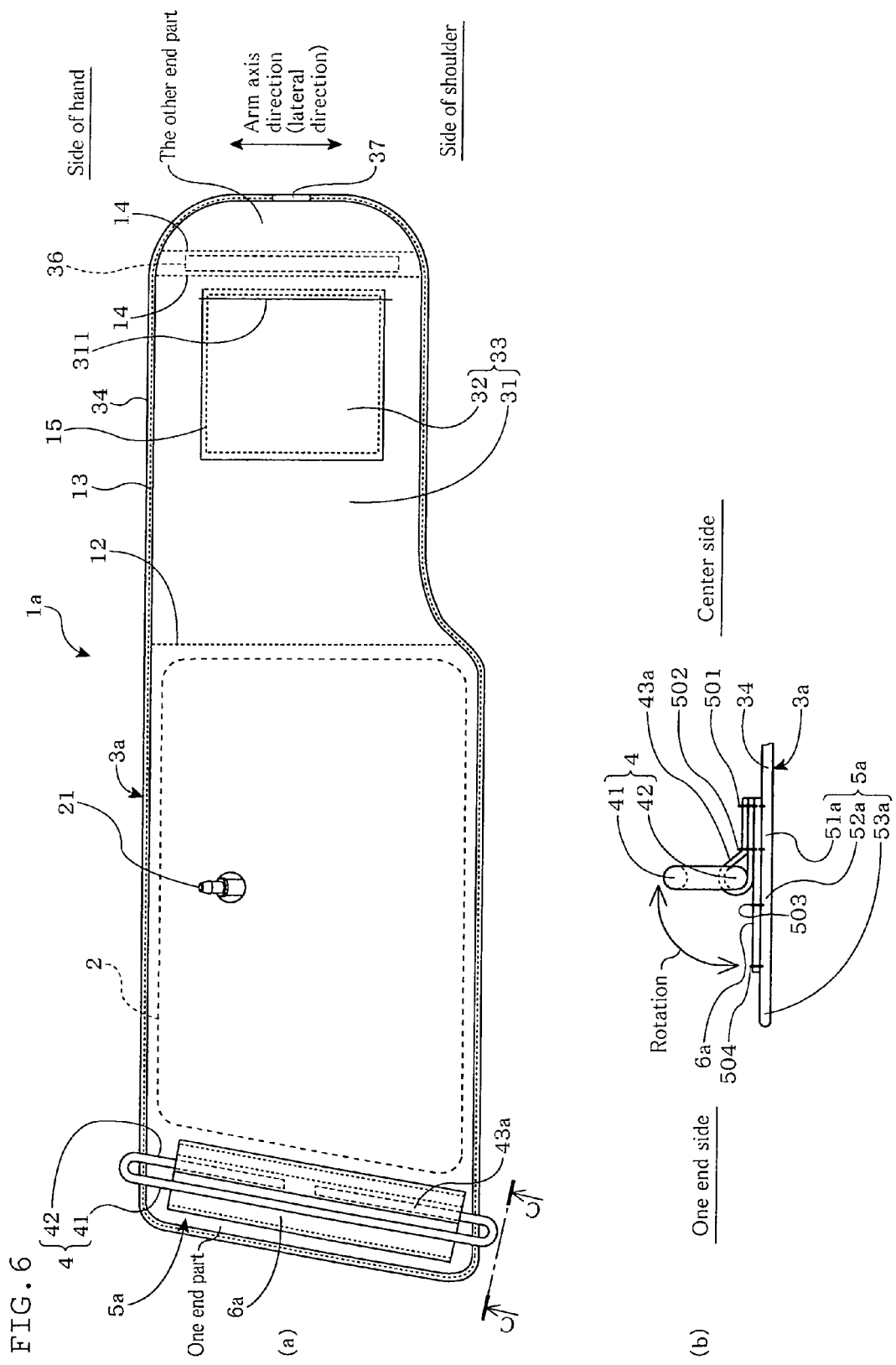
FIG. 6 is a schematic view of the body compressor according to a second embodiment of the present invention, in which (a) is a front development reduced view and (b) is an enlarged view taken along the arrow C-C.

FIG. 6 is a schematic view of the body compressor according to the second embodiment of the present invention, in which (a) is a front development reduced view and (b) is an enraged view taken along the arrow C-C.

In FIG. 6, a body compressor 1a of this embodiment differs from the body compressor 1 of the first embodiment in that a reinforcing member 6a and a fixing member 43a are formed of different members. The other configurations of the body compressor 1a of this embodiment are almost similar to those of the body compressor 1.

Therefore, in FIG. 6, the same parts as those in FIGS. 1 and 2 are indicated by the same symbols, and a detailed explanation thereof is omitted.

In this embodiment, a fixing member 43a having substantially the same width as that of a band-like body 3a is hung on the fixed part 42, and the both ends of the fixing member 43a are stitched to the band-like body 3a with the thread 501 and the thread 502 via part of the reinforcing member 6a at a position nearer to the center than the fixed part 42. This fixing member 43a is made of a fabric or sheet-like member with a prescribed strength and fixes the metal clip 4 in a rotatable manner.

The reinforcing member 6a is made of a fabric or sheet-like member different from that of the loop sheet 31, and serves to allow the bending rigidity of the skin pinching prevention tag part 5 on the center side (a center-side part 51a and an intermediate part 52a) to be higher than the bending rigidity of the skin pinching prevention tag part 5 on the front side (a front-side part 53a).

As explained hereinabove, almost similar to the body compressor 1, attachability (for example, lowered pulling strength, prevention of loose contact, smooth winding free from the feel of resistance or the feel of hitching, or the like) can be significantly improved also by the body compressor 1a of this embodiment.

In addition, since the reinforcing member 6a and the fixing member 43a are formed of different members, freedom in selecting members can be enhanced.

Third Embodiment of the Body Compressor

Figure 7:
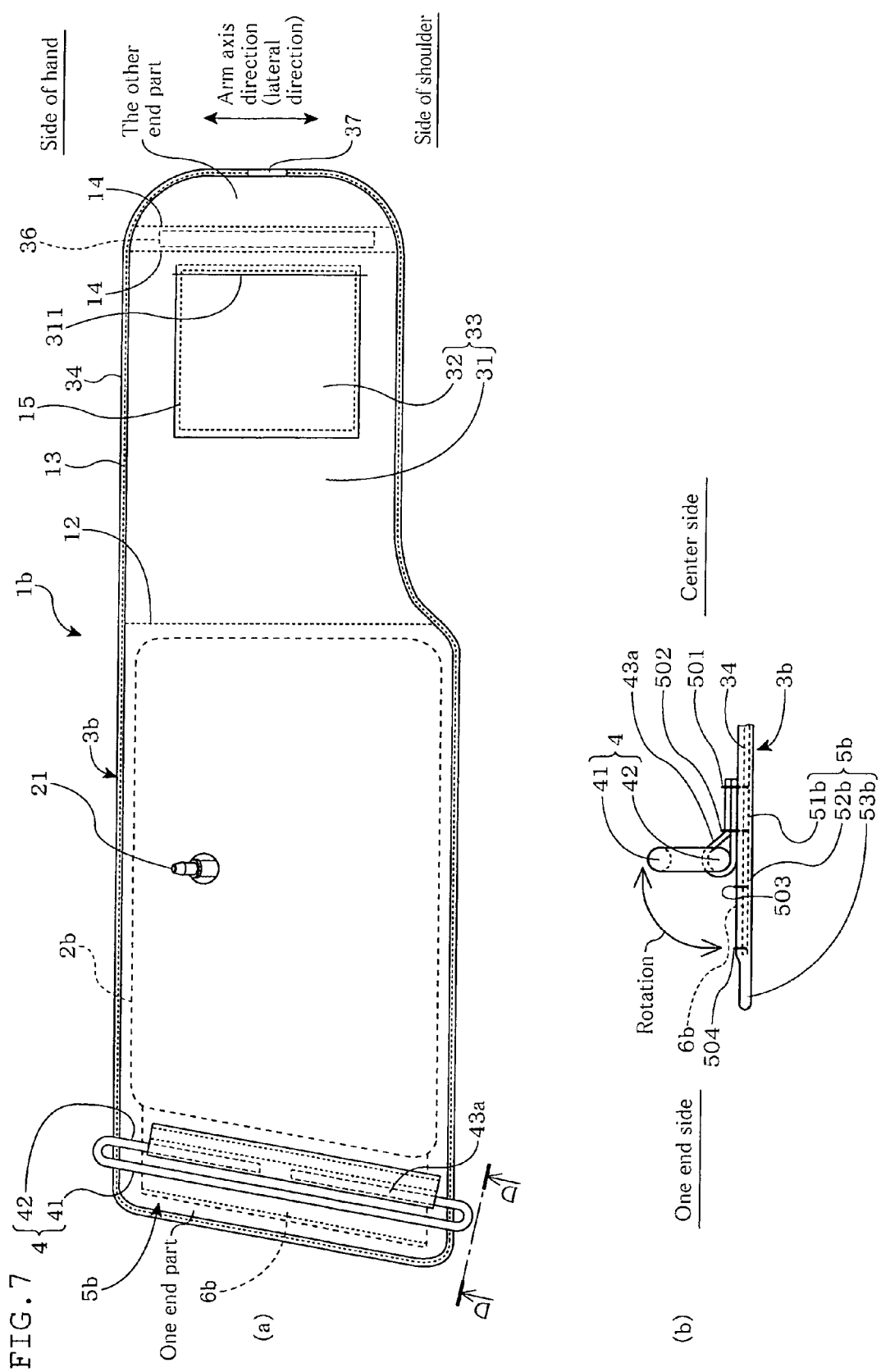
FIG. 7 is a schematic view of the body compressor according to a third embodiment of the present invention, in which (a) is a front development reduced view and (b) is an enlarged view taken along the arrow D-D.

FIG. 7 is a schematic view of the body compressor according to the third embodiment of the present invention, in which (a) is a front development reduced view and (b) is an enlarged view taken along the arrow D-D.

In FIG. 7, a body compressor 1b of this embodiment differs from the body compressor 1a of the second embodiment in that, for example, instead of the reinforcing member 6a, the front part of a fluid bag 2b on the one end side is allowed to function as a reinforcing member. Other configurations of the body compressor 1b of this embodiment are almost similar to those of the body compressor 1a.

Therefore, in FIG. 7, the same parts as those in FIG. 6 are indicated by the same symbols, and a detailed explanation thereof is omitted.

The fluid bag 2b is a substantially trapezoidal bag. The bag has an upper surface sheet which is provided with the joint 21 at almost the center thereof, a lower surface sheet, a welding part at which peripheral parts of these sheets are welded, or the like. The lower surface sheet of this embodiment has a part having almost the similar shape as the upper surface sheet and a substantially parallelogram-shaped part which is extended towards the one end side. This substantially parallelogram-shaped part serves as a reinforcing member 6b.

The above-mentioned reinforcing member 6b is a member which serves to allow the bending rigidity of the skin pinching prevention tag part 5b on the central side (the center-side part 51b and the intermediate part 52b) to be higher than the bending rigidity of the skin pinching prevention tag part 5 on the front side (the front-side part 53b).

In the reinforcing member 6b, the front part on the one end side is positioned between a position at which the fixing member 43a is fixed (the position of the thread 502) and the front part on the one end side of the band-like body 3b. That is, the reinforcing member 6b is stitched to the loop sheet 31 in such a manner that it is away from the one end of the band-like body 3b for a predetermine distance and is parallel with the metal clip 4.

Regarding the above-mentioned stitching, the loop sheet 31 and one end of the reinforcing member 6b are stitched with the thread 504. The loop sheet 31 and the reinforcing member 6b are stitched with the thread 503 on the one end side of the fixed part 42. A pair of parts of the fixing member 43a, which are overlapped each other, the loop sheet 31 and the reinforcing member 6b are stitched with the thread 502 on the center side of the fixed part 42. The both sides of the fixing member 43a, the loop sheet 31 and the reinforcing member 6b are stitched with the thread 501.

As explained hereinabove, almost similar to the body compressor 1a, attachability (for example, lowered pulling strength, prevention of loose contact, smooth winding free from the feel of resistance or the feel of hitching, or the like) can be significantly improved also by the body compressor 1b of this embodiment.

Further, since the reinforcing member 6b is interposed between the loop sheet 31 and the inner surface cover 35 so as not to be exposed outside, the appearance of the body compressor can be improved.

In addition, as compared with the body compressor 1a, since the number of components can be decreased, the production cost can be decreased.

In this embodiment, the substantially parallelogram-shaped part of the lower surface sheet of the fluid bag 2b is allowed to serve as the reinforcing member 6b. The configuration is, however, not limited thereto. Although not shown, the upper surface sheet may also have a substantially parallelogram-shaped part, and the two substantially parallelogram-shaped parts may serve as the reinforcing member 6b. It is also possible to extend the upper surface sheet and the lower surface sheet, which are of a trapezoidal shape, to the one end side, and to allow the thus extended part (this part expands or shrinks by the supply or discharge of air) to function as the reinforcing member 6b.

Fourth Embodiment of the Body Compressor

Figure 8:
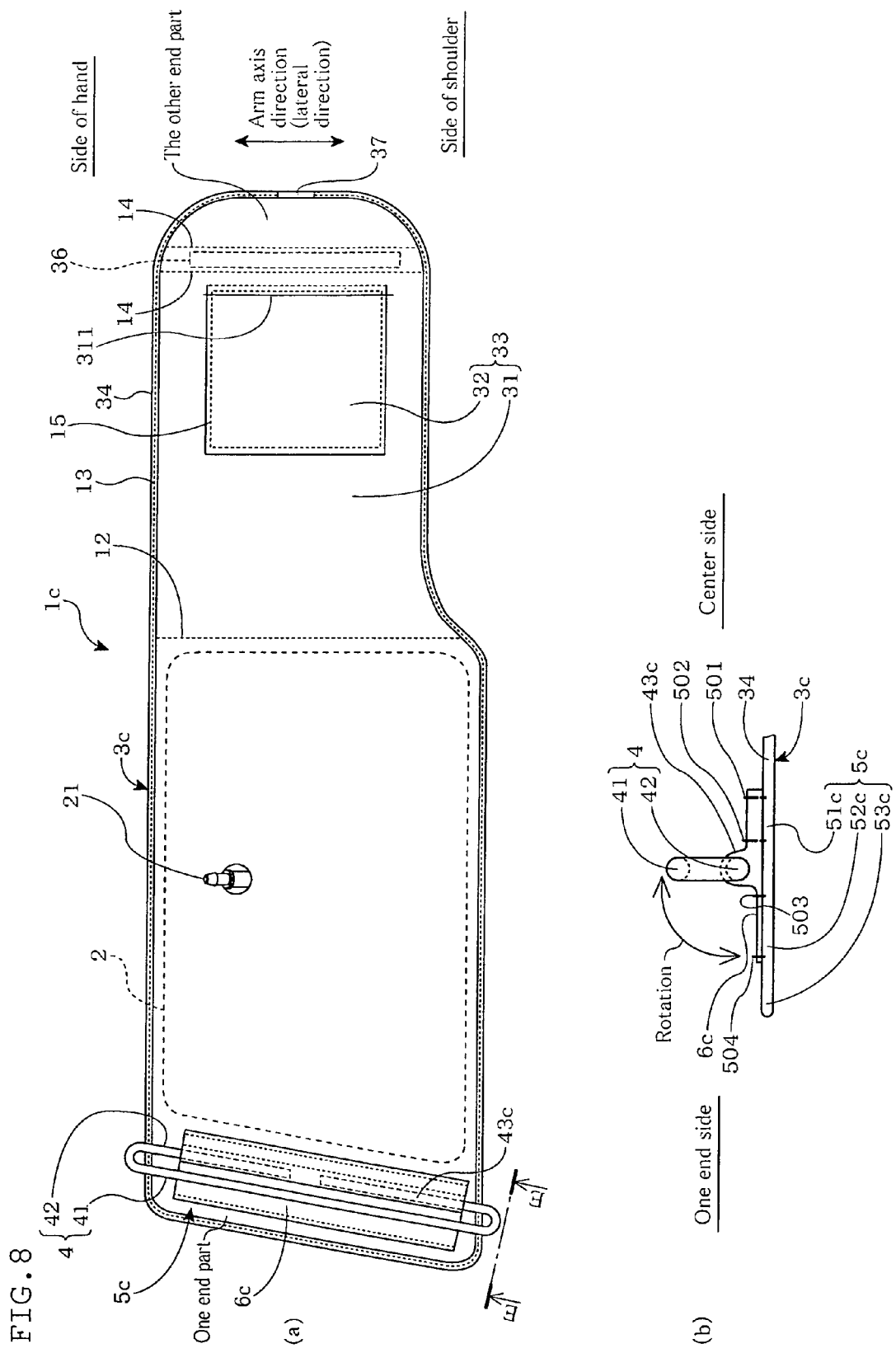
FIG. 8 is a schematic view of the body compressor according to a fourth embodiment of the present invention, in which (a) is a front development reduced view and (b) is an enlarged view taken along the arrow E-E.

FIG. 8 is a schematic view of the body compressor according to the fourth embodiment of the present invention, in which (a) is a front development reduced view and (b) is an enlarged view taken along the arrow E-E.

In FIG. 8, a body compressor 1c of this embodiment differs from the body compressor 1 of the first embodiment that a reinforcing member 6c and a fixing member 43c are integrally formed. The other configurations of the body compressor 1c of this embodiment are almost similar to those of the body compressor 1.

Therefore, in FIG. 8, the same parts as those in FIGS. 1 and 2 are indicated by the same symbols, and a detailed explanation thereof is omitted.

The reinforcing member 6c and the fixing member 43c are made of a resin and are integrally formed.

The reinforcing member 6c has a shape almost similar to that of the reinforcing member 6, and is stitched to a position which is almost the same as the position at which the reinforcing member 6 is stitched. In the reinforcing member 6c, a part on the center side (a part between the thread 503 and the thread 501) is thicker than a part on the one end side (a part between the thread 504 and the thread 503).

Further, in substantially the middle thereof (namely, a part between the thread 502 and the thread 503), a fixing member 43c is formed. The fixing member 43c has a through hole into which the fixed part 42 is inserted. Due to the presence of the fixing member 43c, the fixed part 42 of the metal clip 4 is positioned above the outer surface of a skin pinching prevention tag part 5c (in this embodiment, the upper surface of a part on the other end side of the reinforcing member 6c). Therefore, as mentioned above, when the body compressor 1c is wound around the upper arm 10, friction force can be reduced, whereby the pulling strength can be reduced.

The skin pinching prevention tag part 5c has, from the center side to the one end side, a center-side part 51c, an intermediate part 52c and a front-side part 53c. The center-side part 51c is a part between the thread 501 and the thread 503, and is formed of the thread 501, the thread 502, the thread 503, a part of the reinforcing member 6c on the center side, the fixing member 43c and the band-like body 3c. The intermediate part 52c is a part between the thread 503 and the thread 504, and is formed of the thread 503, the thread 504, part of the reinforcing member 6c on the one end side and the band-like body 3c. Further, the front-side part 53c is a part nearer to the one end side than the thread 504, and is formed of the band-like body 3c.

The skin pinching prevention tag part 5c has a rigidity satisfying the following relationship: the rigidity of the center-side part 51c>the rigidity of the intermediate part 52c>the rigidity of the front-side part 53c. That is, in the skin pinching prevention tag part 5c, since the center-side part 51c is reinforced by the fixing member 43c, the reinforcing member 6c or the like, the intermediate part 52c is reinforced by the reinforcing member 6c or the like, and the front-side part 53c is formed of the band-like body 3c, it has bending rigidity differing in three stages.

As explained hereinabove, almost similar to the body compressor 1, attachability (for example, lowered pulling strength, prevention of loose contact, smooth winding free from the feel of resistance or the feel of hitching, or the like) can be significantly improved also by the body compressor 1c of this embodiment.

In addition, since the reinforcing member 6c is integrally formed with the fixing member 43c and the thickness or the like thereof can be freely determined, attachability or the like can be further improved.

Further, as compared with the body compressor 1a, since the number of components can be decreased, the production cost can be reduced.

Fifth Embodiment of the Body Compressor

Figure 9:
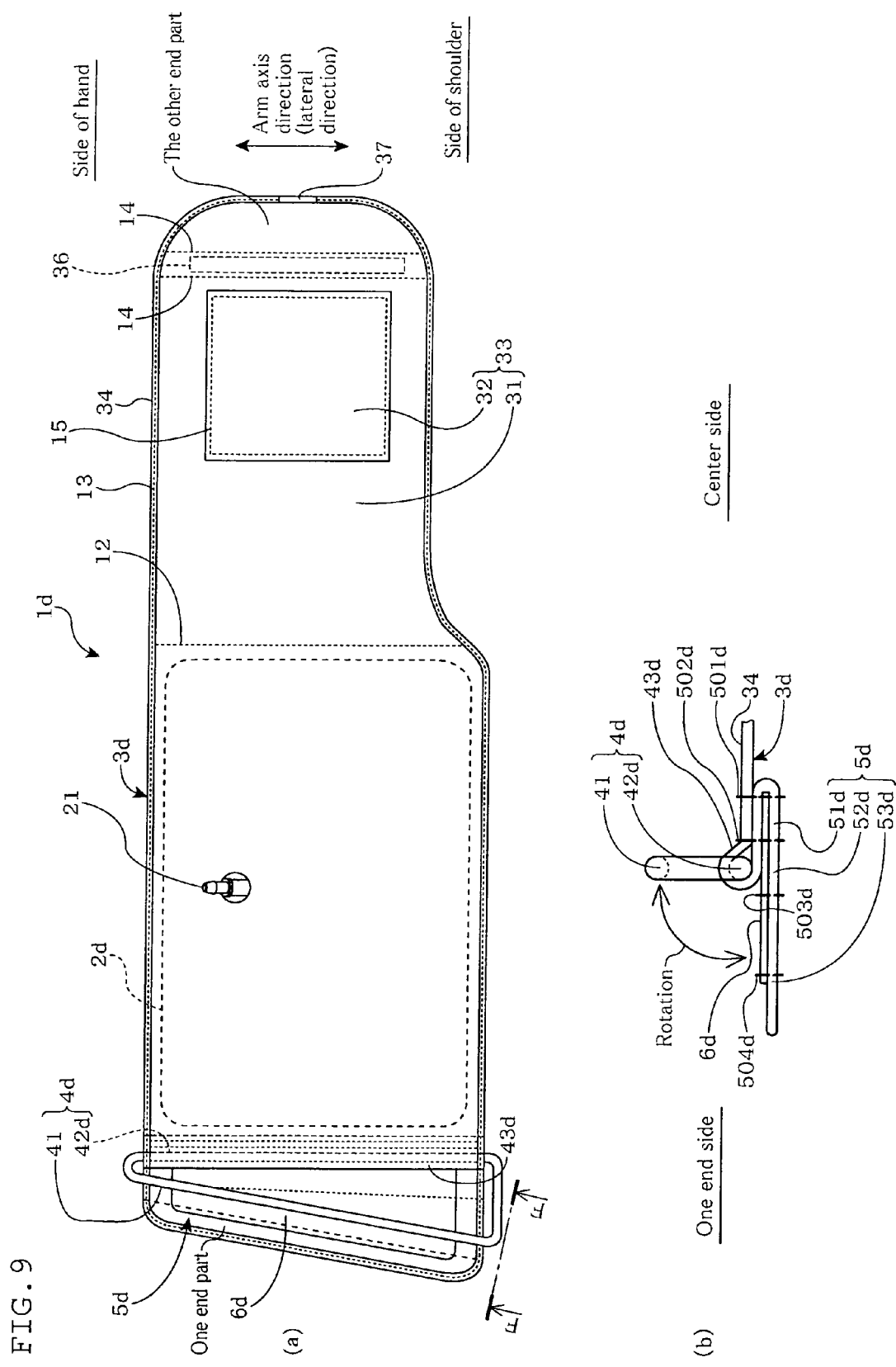
FIG. 9 is a schematic view of the body compressor according to a fifth embodiment of the present invention, in which (a) is a front development reduced view and (b) is an enlarged view taken along the arrow F-F.

FIG. 9 is a schematic view of the body compressor according to the fifth embodiment of the present invention, in which (a) is a development reduced view and (b) is an enlarged view taken along the arrow F-F.

In FIG. 9, a body compressor 1d of this embodiment differs from the body compressor 1a of the second embodiment in that, for example, a fixing member 43d is formed of a folded part of a band-like body 3d. The other configurations of the body compressor 1d of this embodiment are almost similar to the body compressor 1a.

Therefore, in FIG. 9, the same parts as those in FIG. 6 are indicated by the same symbols, and a detailed explanation thereof is omitted.

The fluid bag 2d is a substantially rectangular bag. The hook sheet 32 is attached in substantially the same manner as in the case of the body compressor 101.

A metal clip 4d is a piece of round steel which is formed in a substantially right-angled triangle shape and has the hanging part 41 and a fixed part 42d.

The metal clip 4d is attached to the band-like body 3d by the fixing member 43d formed of the folded part of the band-like body 3d such that the fixed part 42d is positioned above the outer surface of a skin pinching prevention tag part 5d (in this embodiment, the upper surface of the reinforcing member 6d).

Specifically, the one end part of the band-like body 3d is folded towards to the center side in a state in which it is hung on the fixed part 42d, and then folded towards the one end side with the reinforcing member 6d being interposed such that the center-side part 51d is formed. The thus folded band-like body 3d is stitched with a thread 501d and a thread 502d. As a result, when the body compressor 1d is wound around the upper arm 10, friction force can be decreased, whereby the force required for pulling can be significantly decreased. In addition, since the number of components can be reduced and operability in stitching can be enhanced, the production cost can be decreased.

The reinforcing member 6d is formed of a fabric or sheet-like member, and has a trapezoidal shape having almost the same width as that of the band-like body 3d. This reinforcing member 6d is a member which conduct reinforcement in order to allow the bending rigidity of the skin pinching prevention tag part 5d on the center side (the center-side part 51d and the intermediate part 52d) to be higher than the bending rigidity on the front side (front-side part 53d).

In the reinforcing member 6d, the front part thereof on the one end side is positioned between the installation position of the fixing member 43d (the position of the thread 502d) and the one end part of the band-like body 3d. That is, the reinforcing member 6d is stitched to the band-like body 3d in a state that it is away from the one end of the band-like body 3d for a predetermined distance.

Regarding the above-mentioned stitching, one end of the reinforcing member 6d and the band-like body 3d are stitched with the thread 504. The reinforcing member 6d and the band-like body 3d are stitched with the thread 503d on the one end side of the fixed part 42d. The pair of fixing members 43d which are overlapped one on itself (a pair of the band-like bodies 3d), the reinforcing member 6d and the band-like body 3d are stitched with a thread 502d on the center side of the fixed part 42d. The both sides of the fixing member 43d (a pair of the band-like bodies 3d), the other end part of the reinforcing member 6d and the band-like body 3d are stitched with a thread 501d.

The skin pinching prevention tag part 5d has, from the center side to the one end side, a center-side part 51d, an intermediate part 52d and a front-side part 53d. The center-side part 51d is a part between a thread 501d and a thread 502d, and is formed of the thread 501d, the thread 502d, the pair of the band-like body 3d, the reinforcing member 6d and the band-like body 3d. The intermediate part 52d is a part between the thread 502d and the thread 504d, and is formed of the thread 502d, the thread 503d, the thread 504d, the reinforcing member 6d and the band-like body 3d. Further, the front-side part 53d is a part nearer to the one end side than the thread 504d, and is formed of the band-like body 3d.

The skin pinching prevention tag part 5d has a rigidity satisfying the following relationship: the rigidity of the center-side part 51d>the rigidity of the intermediate part 52d>the rigidity of the front-side part 53d. That is, in the skin pinching prevention tag part 5d, since the center-side part 51d is reinforced by the pair of band-like body 3d, the reinforcing member 6d or the like, the intermediate part 52d is reinforced by the reinforcing member 6d or the like, and the front-side part 53d is formed of the band-like body 3d, it has bending rigidity differing in three stages.

As explained hereinabove; almost similar to the body compressor 1, attachability (for example, lowered pulling strength, prevention of loose contact, smooth winding free from the feel of resistance or the feel of hitching, or the like) can be significantly improved also by the body compressor 1d of this embodiment.

[One Embodiment of a Blood Pressure Measurement Apparatus]

The present invention is also effective as an invention of a blood pressure measurement apparatus (hereinafter appropriately abbreviated as a "blood pressure monitor").

Figure 10:
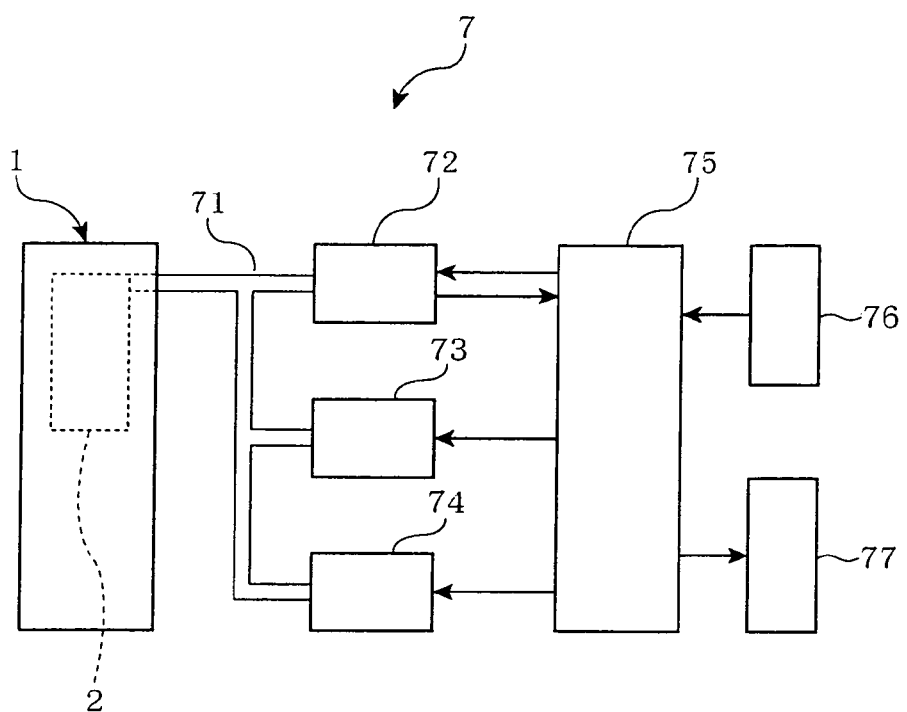
FIG. 10 is a schematic block diagram of essential parts of an oscillometric electronic blood monitor according to one embodiment of the present invention.
Figure 11:
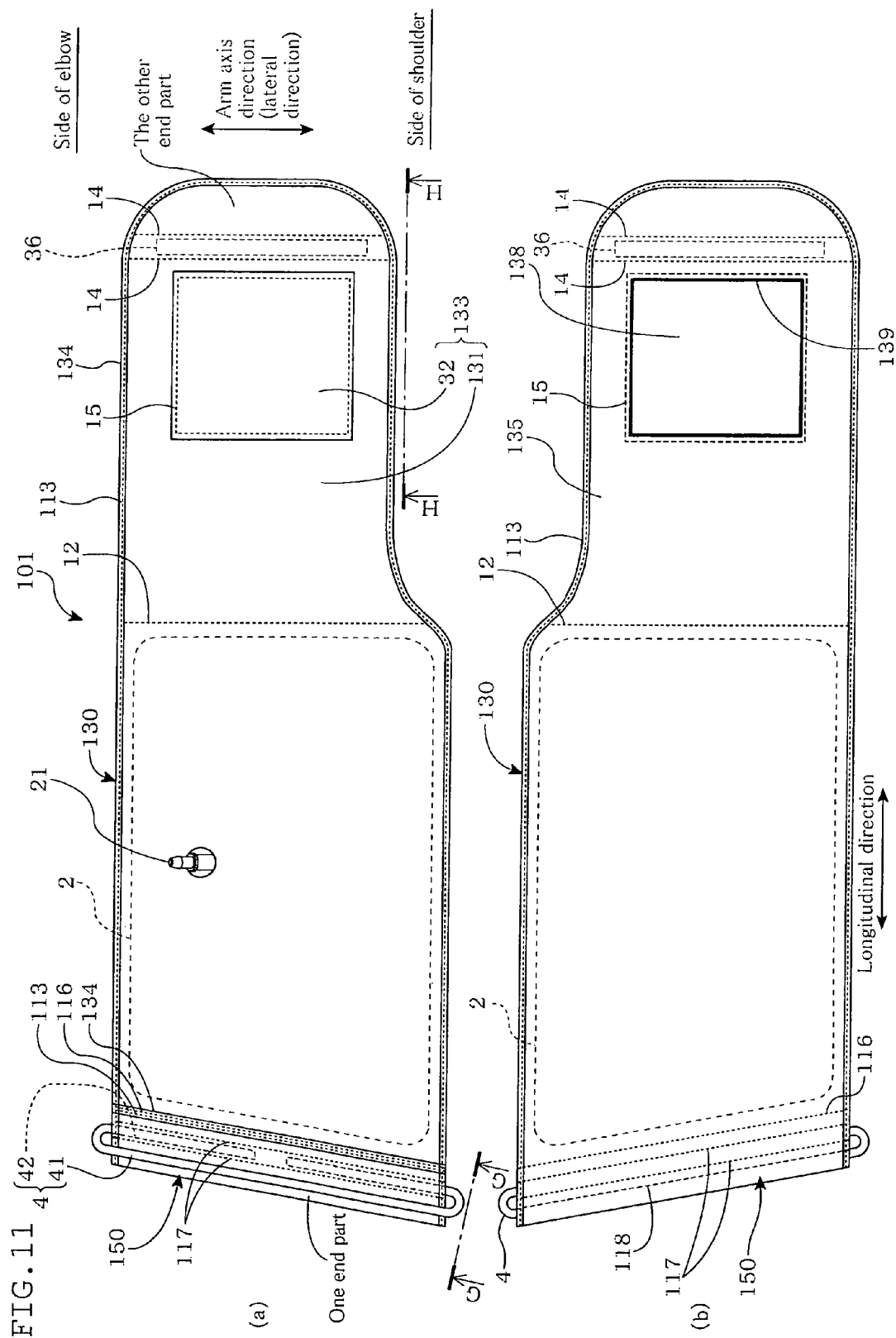
FIG. 11 is a schematic reduced view of a conventional body compressor, in which (a) is a front development view and (b) is a rear development view.
Figure 12:
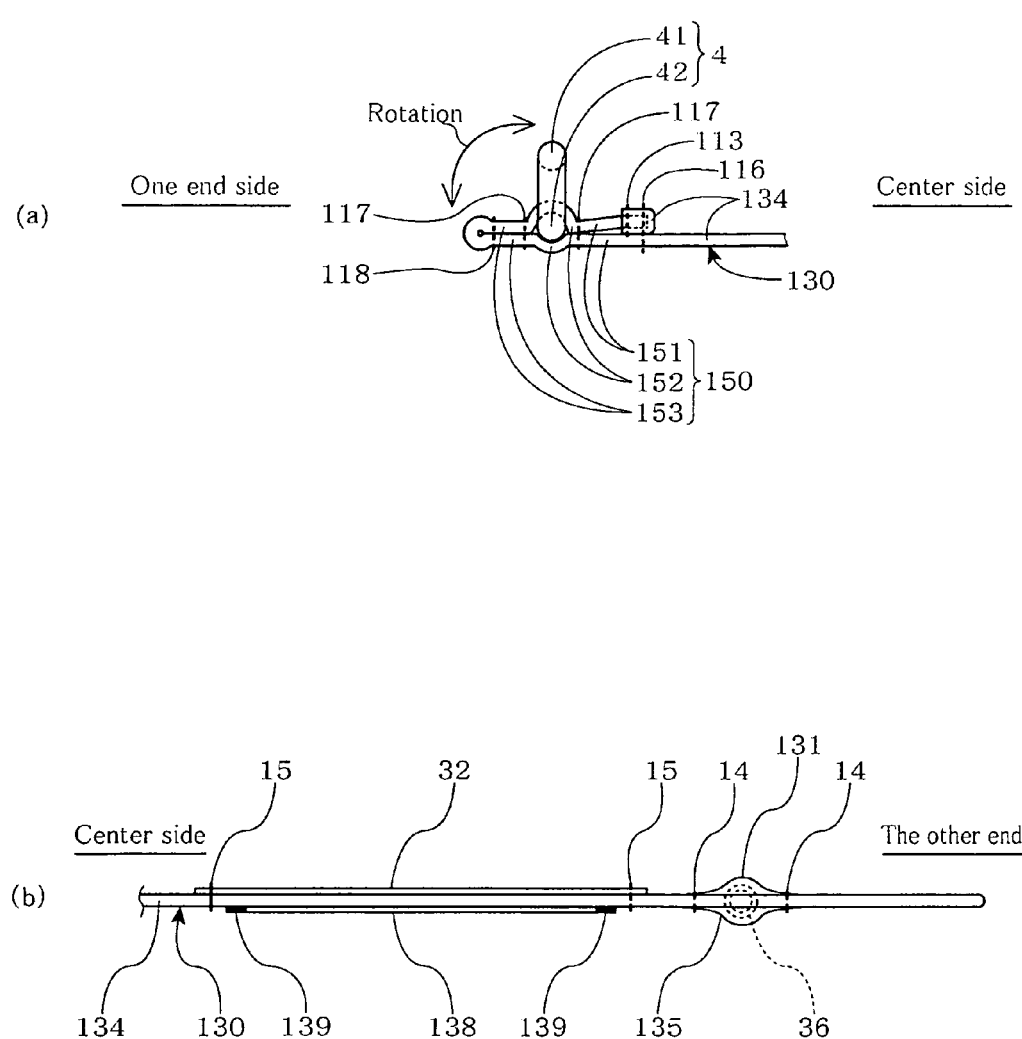
FIG. 12 is a schematic view of a conventional body compressor, in which (a) is a view taken along the arrow G-G and (b) is a view taken along the arrow H-H.
Figure 13:
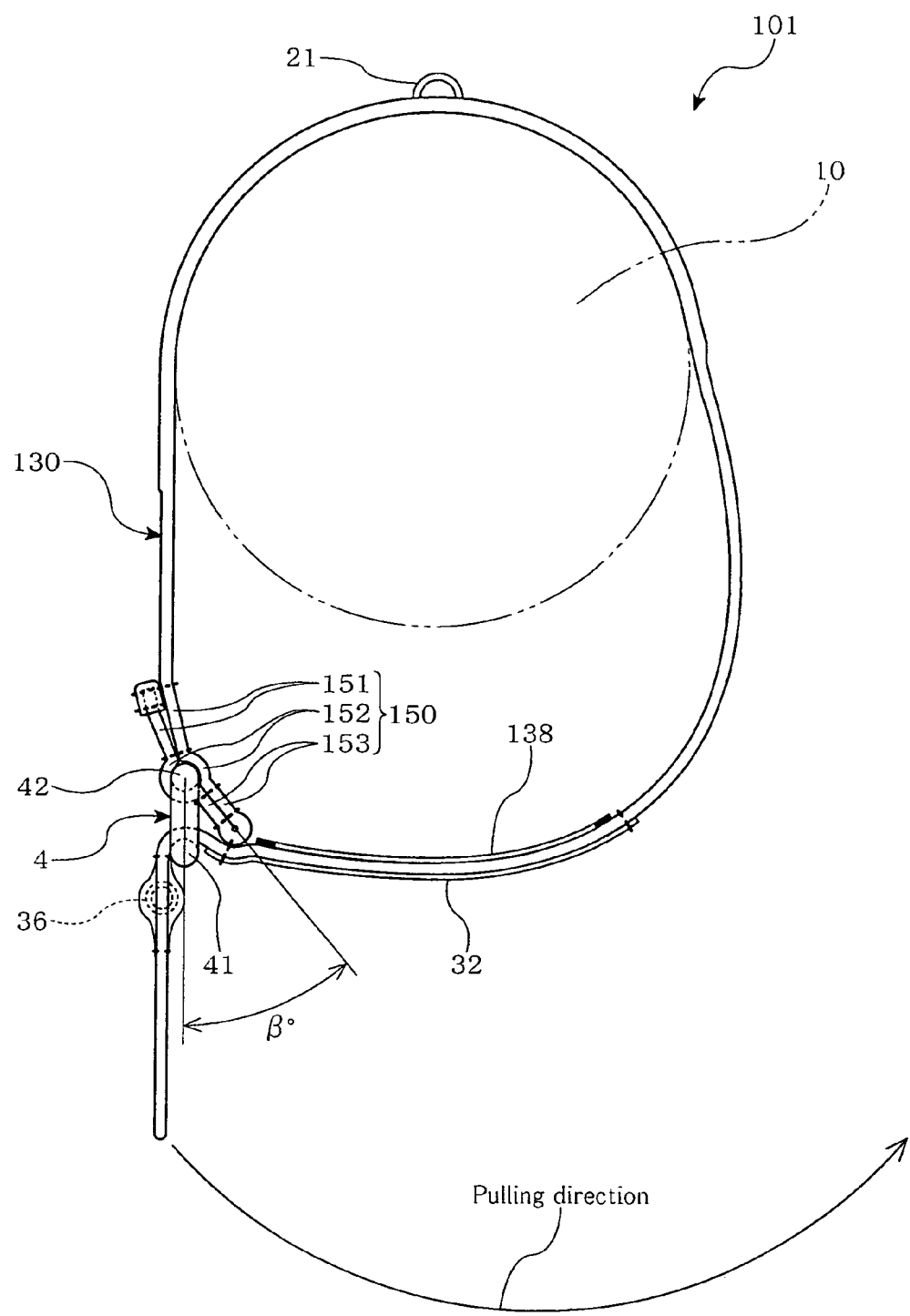
FIG. 13 is a schematic view of a conventional body compressor for explaining the operation at the start of winding.

FIG. 10 is a schematic block diagram of essential parts of an oscillometric electronic blood monitor according to one embodiment of the present invention.

In FIG. 10, an oscillometric electronic blood monitor 7 is formed of the body compressor 1 with the built-in air bag 2, a pressure sensor 72, a pump 73 and an exhaust valve 74 which are intercommunicated with the air bag 2 through a tube 71, an information processing apparatus 75 connected with the pressure sensor 72, the pump 73 and the exhaust valve 74, and an operation switch 76 and a display 77 which are connected with the information processing apparatus 75.

Here, the oscillometric electronic blood monitor 7 of this embodiment has a configuration in which it is provided with the above-mentioned body compressor 1.

Due to such a configuration, as mentioned above, the oscillometric electronic blood monitor 7 of this embodiment can have significantly improved attachability (for example, lowered pulling strength, prevention of loose contact, smooth winding free from the feel of resistance or the feel of hitching, or the like). Due to the improvement of attachability, a user can attach the body compressor 1 easily at a predetermined position, whereby reliability of blood pressure measurement can be improved.

Hereinabove, the body compressor and the blood pressure measurement apparatus of the present invention are explained with reference to preferred embodiments thereof. The body compressor and the blood pressure measurement apparatus of the present invention are not limited to the above-mentioned embodiments. It is needless to say that various modifications are possible within the scope of the present invention.

For example, a sheet-like member or the like is used as a reinforcing member in each of the above-mentioned embodiments. The reinforcing member is not limited to such sheet-like member, and a thread used for stitching or an adhesive or the like may be used, for example.

The body compressor in each of the above-mentioned embodiments has a configuration in which it is normally attached to the upper arm. The position to which the body compressor is attached is not limited to the upper arm. For example, the body compressor in each of the above-mentioned embodiments can be used in a wrist blood pressure monitor in which a body compressor is attached to the wrist.

Further, the body compressor used in a wrist blood pressure monitor may have a configuration in which an air bag is extended from one end of a band-like body to the other end thereof.

INDUSTRIAL APPLICABILITY

As described above, the body compressor of the present invention is not exclusively used in a blood pressure monitor cuff. For example, the present invention can also be effectively applied to a stanching body compressor which requires an accurate measurement of a pulse wave during pressure elevation.

Some embodiments and/or examples of the present invention are described in detail above. A person skilled in the art can easily make many modifications to the embodiments and/or examples which are given as exemplifications. Therefore, these modifications can be included within the scope of the present invention.

The contents of the above-mentioned documents and the Japanese Patent Application No. 2009-102682 on the base of which the priority is claimed are herein incorporated by reference in its entirety.

The invention claimed is:

1. A body compressor configured to be wound around a human body, comprising:
   a fluid bag which expands and shrinks due to supply and discharge of a fluid;
   a band-like body for accommodating the fluid bag;
   a reinforcing element attached to the band-like body;
   a fixing element attached to the reinforcing element; and
   a metal clip comprising a hanging part on one end and a fixed part on another end, wherein
   the metal clip is provided on one end part of the band-like body, the other end at part of the band-like body is inserted into the metal clip, and the metal clip is disposed above an upper surface of the reinforcing element,
   a metal clip-fixing position is a position where a distance from an end of the one end part of the band-like body to the metal clip-fixing position is longer than a distance from the hanging part of the metal clip to the fixed part of the metal clip,
   the reinforcing element extends from a position closer to a center part of the band-like body than the metal clip-fixing position to a position adjacent to the hanging part of the metal clip when the metal clip rotates away from the center part of the band-like body,
   the fixing element fixing the metal clip, disposed on the position closer to the center part of the band-like body than the metal clip-fixing position and hung on the fixed part of the metal clip, and two ends of the fixing element are attached to the band-like body through a part of the reinforcing element at the position closer to the center part of the band-like body than the metal clip-fixing position,
   an end of the reinforcing element is positioned between the metal clip-fixing position and the end of the one end part of the band-like body and adjacent to the hanging part of the metal clip when the metal clip rotates away from the center part of the band-like body,
   a rigidity of a part of the reinforcing element and the band-like body extending from the end of the reinforcing element to the metal-clip fixing position is higher than a rigidity of a part of the band-like body extending from the end of the one end part of the band-like body to the end of the reinforcing element, and
   a rigidity of a part of the reinforcing element and the band-like body present on a side closer to the center part of the band-like body than the metal clip-fixing position and corresponding to the fixing element is higher than the rigidity of the part of the reinforcing element and the band-like body extending from the end of the reinforcing element to the metal-clip fixing position.

2. The body compressor according to claim 1, wherein the reinforcing element and the fixing element are integrally formed.

3. The body compressor according to claim 1, wherein a part of the band-like body which is folded and layered comprises the fixing element.

4. The body compressor according to claim 1, wherein the fixing element is present between the metal clip and the end of the reinforcing element on the position closer to the center part of the band-like body than the metal clip-fixing position.

5. The body compressor according to claim 4, wherein another end of the reinforcing element is positioned between the end of the one end part of the band-like body and an end of the hanging part of the metal clip.

6. A blood pressure measurement apparatus, comprising:
   a body compressor configured to be wound around a human body, comprising
   a fluid bag which expands and shrinks due to supply and discharge of a fluid;
   a band-like body for accommodating the fluid bag;
   a reinforcing element attached to the band-like body;
   a fixing element attached to the reinforcing element;
   a metal clip comprising a hanging part on one end and a fixed part on another end;
   a pressure sensor connected to the fluid bag;
   a pump connected to the fluid bag;
   an exhaust valve connected to the fluid bag; and
   an information processing apparatus comprising an operation switch and a display, and connecting the pressure sensor, the pump, and the exhaust valve with each other,
   wherein the metal clip is provided on one end part of the band-like body, the other end part of the band-like body is inserted into the metal clip, and the metal clip is disposed above an upper surface of the reinforcing element,
   a metal clip-fixing position is a position where a distance from an end of the one end part of the band-like body to the metal clip-fixing position is longer than a distance from the hanging part of the metal clip to the fixed part of the metal clip,
   the reinforcing element extends from a position closer to a center part of the band-like body than the metal clip-fixing position to a position adjacent to the hanging part of the metal clip when the metal clip rotates away from the center part of the band-like body,
   the fixing element fixing the metal clip, disposed on the position closer to the center part of the band-like body than the metal clip-fixing position and hung on the fixed part of the metal clip, and two ends of the fixing element are attached to the band-like body through a part of the reinforcing element at the position closer to the center part of the band-like body than the metal clip-fixing position, an end of the reinforcing element is positioned between the metal clip-fixing position and the end of the one end part of the band-like body and adjacent to the hanging part of the metal clip when the metal clip rotates away from the center part of the band-like body, a rigidity of a part of the reinforcing element and the band-like body extending from the end of the reinforcing element to the metal-clip fixing position is higher than a rigidity of a part of the band-like body extending from the end of the one end part of the band-like body to the end of the reinforcing element, and a rigidity of a part of the reinforcing element and the band-like body present on a side closer to the center part of the band-like body than the metal clip-fixing position and corresponding to the fixing element is higher than the rigidity of the part of the reinforcing element and the band-like body extending from the end of the reinforcing element to the metal-clip fixing position.

* * * * *